United States Patent [19]

Spickett et al.

[11] Patent Number: 5,288,506
[45] Date of Patent: Feb. 22, 1994

[54] ANTACID COMPOSITIONS WITH PROLONGED GASTRIC RESIDENCE TIME

[75] Inventors: Robert G. W. Spickett; Jose L. F. Vidal; Juan C. Escoi, all of Barcelona, Spain

[73] Assignee: Walton S.A., Madrid, Spain

[21] Appl. No.: 340,780

[22] Filed: Apr. 20, 1989

[30] Foreign Application Priority Data

Apr. 21, 1988 [GB] United Kingdom ............... 8809421

[51] Int. Cl.$^5$ .................. A61K 9/16; A61K 9/20; A61K 9/54
[52] U.S. Cl. .................... 424/498; 424/441; 424/465; 424/468; 424/489; 424/490; 424/497; 424/470; 514/819; 514/925
[58] Field of Search ............ 424/489, 490, 492, 470, 424/469, 441, 498

[56] References Cited

U.S. PATENT DOCUMENTS 4,101,650  7/1978  Umezawa ............... 424/490
4,199,560  4/1980  Gyarmati et al. ......... 424/470
4,844,905  7/1989  Ichikawa et al. ......... 424/494

FOREIGN PATENT DOCUMENTS 8800051  1/1988  World Int. Prop. O. .

OTHER PUBLICATIONS

United States Adopted Names (USAN) and United States Pharmacopeia (USP) Dictionary of Drug Names, pp. 31, 301 and 354 (1991).

Primary Examiner—Thurman K. Page
Assistant Examiner—James M. Spear
Attorney, Agent, or Firm—Spencer, Frank & Schneider

[57] ABSTRACT

Antacid powders, tablets etc. of prolonged gastric residence time have an internal phase of a solid antacid and excipient surrounded by a solid external phase containing a hydrophobic substance e.g. an ester of glycerol with palmitic or stearic acid, a hydroxylated polyalkene and a non-ionic emulsifier.

10 Claims, No Drawings

ANTACID COMPOSITIONS WITH PROLONGED GASTRIC RESIDENCE TIME

BACKGROUND OF THE INVENTION

1. Field of the Invention

This invention relates to antacid compositions having a prolonged gastric residence time.

2. Technical Review

Classical antacids such as aluminium and magnesium hydroxide gels and co-gels and the new crystalline aluminium magnesium hydroxycarbonates or sulphates such as Hydrotalcite, Almagate and Magaldrate are either rapidly neutralized to water soluble ions or sediment in the fundus of the stomach, and are evacuated into the duodenum by normal peristalsis with subsequent loss of unused drug from its site of action. Consequently they do not neutralize the continuous output of hydrochloric acid by the parietal cells in the human stomach for a prolonged period of time.

SUMMARY OF THE INVENTION

The present invention provides solid oral pharmaceutical preparation with protracted action consisting of an internal phase of discrete solid granules containing the active antacid ingredient and a solid external phase surrounding the said granules. The internal phase consists of a powder mixture containing the active antacid ingredient and pharmaceutically acceptable excipients and the external phase contains a hydrophobic organic substance, particularly stearic, or palmitic acid esters, a hydroxylated polyalkene polymer and a non-ionic emulsifier.

The preparations described in this invention do not sediment to the fundus of the stomach, are more slowly evacuated to the duodenum by peristalsis and are available in the stomach to neutralise the hydrochloric acid secreted by the parietal cells for a prolonged period of time, and consequently resolve an important problem in the field of antacid therapy.

DETAILED DESCRIPTION OF THE PREFERRED EMBODIMENTS

It is well known that hyperacidity alone does not cause ulcers, but can be a factor in their formation, and can also inhibit healing of preformed ulcers. However, it is desirable that hyperacidity be reduced and an antacid should satisfy the following criteria:

The neutralizing effect must be rapid and maintained during normal digestion time in the stomach.
It must neutralise the required amount of acid.
It must raise the pH value of the gastric contents to a level at which pepsin activity is reduced but not fully inhibited.
It should not cause the gastric pH to rise above 6.
It should not cause systemic alkalosis even when administered repeatedly.
The antacid should not be emptied into the duodenum until it has exerted its full effect in the stomach.

The present invention includes two-phase solid oral pharmaceutical compositions: e.g. in the form of powder, tablets (effervescent, chewable), coated tablets or capsules, with prolonged antacid activity. The composition may be prepared by granulation of a powder mixture containing the active antacid ingredient, a solid carrier and other excipients with an organic emulsion containing hydrophobic and hydrophilic components, to form granules surrounded by an external phase which, owing to its specific physico-chemical properties, prolongs the liberation of the active ingredient thereby augmenting its biological utilization. The resulting granules can then be tableted or filled into capsules. The granulating emulsion may contain as hydrophobic component, for example, esters of 12-hydroxystearic, stearic, or palmitic acid and, as hydrophilic component, a hydroxylated polyalkene polymer. By appropriate selection of the components of the emulsion, particularly the non-ionic surface active agent, e.g. polyoxyethylene sorbitan esters and changing their quantitative ratio, the rate of liberation and gastric residence time of the active ingredient can be modified.

More specifically this invention provides compositions of products with antacid properties in which the active component is a crystalline synthetic antacid such as Almagate, Hydrotalcite, Magaldrate; the compositions may also contain aluminium hydroxide or aluminium magnesium hydroxide cogels, in a vehicle which provides a prolonged gastric residence time. The prolonged residence time is a function of the lipophilicity of the particles which preferentially adhere to the gastric mucosa or form a layer on the surface of the gastric contents. The antacid is then slowly liberated, reacts with hydrogen ions in the vicinity, protects the mucosa and its emptying from the stomach is delayed in spite of peristaltic movements. The invention involves coating the particles of the antacid product with a solid emulsion of selected excipients, which increases the lipophilicity and delays reaction with hydrogen ions without altering the intrinsic acid neutralising properties.

The hydrophilic component of the emulsion can be a hydroxylated polyalkene polymer, with molecular weight 950–10,000, preferably 5000–7000, and the hydrophobic component can be glycerol mono-, di- or tripalmitic or stearic esters, or preferably hydrogenated mono-, di- or triglycerides, especially those containing 70–90% of 12-hydroxystearic acid esters and 10–30% of stearic acid esters. A non-ionic surface active agent, suitable for use with water in oil emulsions can be used as an emulsion stabiliser. The selection of the optimal composition for delaying active ingredient liberation and increasing gastric residence time may be calculated from the hydrophilic-lipophilic balance (HLB) of the components of the granulating emulsion. Non-ionic emulsifiers such as polyoxyethylene-sorbitan-monooleates, polyoxyethylene-sorbitan-mono-laurates, polyoxyethylene-sorbitan-monostearates and mono-palmitates, and preferably sorbitan fatty acid esters (lauric, palmitic, oleic) with a hydrophilic-lipophilic balance lower than 7, generally give satisfactory results if the amount of the hydrophobic component emulsified in the granulating liquid is between 50–90 parts, preferably 80 parts by weight and the hydrophilic component is between 10–20, preferably 13 parts by weight. Such granulating emulsions are expediently prepared by dissolving the hydrophobic component in a convenient amount of chloroform or methylene chloride warming to 30 degrees C., adding the emulsifier to the solution thus obtained, and emulsifying with the hydrophilic compound.

The resulting granulating emulsion can then be used for granulating the powder mixture containing active ingredients, carrier, and optionally other excipients. For example, one part by weight of the powder mixture is admixed and kneaded, preferably with 1.3 parts by weight of granulating emulsion. The wet mass is kneaded again with a solution of a binder, e.g. gelatin, polyvinylpyrrolidone, hydroxypropylcellulose, preferably an aqueous 3% solution of polyvinylpyrrolidone, and finally the wet mass granulated by known methods e.g. by pressing through a sieve. Flavouring substances, disintegrants and lubricating agents, such as cross-linked sodium carboxymethylcellulose and magnesium stearate, can then be added to the dried granules and the mixture pressed into tablets or filled into bottles, individual sachets or hard gelatin capsules.

The preferred pharmaceutical forms for utilization of the preparation of this invention are powders, granulates, or chewable tablets, which may or may not be combined with an adequate amount of uncoated active component to ensure a rapid initial acid neutralization. The dose of antacid (uncoated and coated) should be sufficient to neutralize the acid output of the parietal cell over a prolonged time period by limiting the loss of unused antacid by periodic gastric emptying. With conventional antacids this would only be possible with high doses of the active principles causing gastric pH to rise above 6. In addition loss of unchanged antacid by normal peristalsis into the duodenum where its presence is either not required or unwanted reduces their clinical utility.

The present invention provides:
1) The possibility of administration of higher, and more efficacious doses of antacid with longer intervals between doses.
2) Physical protection of the gastric mucosa against fluctuations of pH.
3) Prolonged antacid effect, favouring patient comfort and compliance.
4) More complete utilization of the adminstered dose by prolonged residence time in the stomach.
5) Reduction of gastro-oesophageal acid reflux due to the presence of a reserve of floating antacid on the surface of the gastric contents.

In an additional aspect of this invention, the above compositions may be combined with substances which inhibit gastric acid secretion, e.g., cimetidine, ranitidine or other $H_2$-antihistamines or proton pump blockers for the treatment of gastrooesophageal reflux disease and gastroduodenal ulcers.

Further details of the present invention are to be found in the following Examples without limiting the scope of the claims to the Examples.

EXAMPLE 1

For the production of a granulate preparation with floating and protracted dissolution properties, the following quantities of substances are used per gram of final product:

| | |
|---|---|
| Hydrotalcite | 0.75 g |
| Hydrophobic silicon dioxide | 0.14 g |
| Sorbitan monooleate 60 | 0.005 g |
| Polyoxyethylene stearate | 0.01 g |
| Castorwax | 0.06 g |
| Polyvinylpyrrolidone | 0.035 g |

The hydrotalcite and hydrophobic silicon dioxide are milled to a particle diameter less than 125 microns, (very fine powder) and are mixed to form a homogeneous mixture, then kneaded successively with granulating liquids A and B prepared as follows:

Granulating Liquid A

Sorbitan monooleate, polyoxyethylene stearate, and castorwax are dissolved in warm (35 degrees C.) methylene chloride.

Granulating Liquid B

Polyvinylpyrrolidone is dissolved, with vigorous stirring in 96% by vol. ethyl alcohol, at room temperature.

The wet mass is passed through a sieve (no 14 ASTM), dried (60 degrees C., air circulating oven), finishing and lubricating substances (e.g. magnesium stearate and Aerosil) are admixed, and the mixture is dosed into multidose plastic bottles.

Utilising the above process, granulate preparations of almagate and magaldrate can be prepared containing 0.75 g of active principal per g. of granulate.

EXAMPLE 2

For the production of chewable tablets the following materials are used:

| | Amount per tablet |
|---|---|
| Magaldrate | 0.75 g |
| Silicon dioxide | 0.14 g |
| Polysorbate 21 | 0.001 g |
| Sorbitan Monooleate 60 | 0.004 g |
| Polyethyleneglycol 400 | 0.02 g |
| Glycerine tripalmitate | 0.06 g |
| Polyvinylpyrrolidone | 0.06 g |
| Mannitol | 0.97 g |

A granulate is prepared as described in Example 1 and is then blended with an auxiliary granulate of mannitol, prepared conventionally using an aqueous solution of polyvinylpyrrolidone as granulating liquid, to improve the flow properties of the powder. The mass is lubricated with e.g. magnesium stearate and tablets are produced in conventional tableting equipment.

Utilising the above process tablets containing 0.75 g of almagate or hydrotalcite can be prepared.

EXAMPLE 3

Chewable tablets containing coated and uncoated antacid are prepared using the following materials:

| | Amount per tablet |
|---|---|
| Almagate (antacid) | 1.5 g |
| Hydrophobic silicon dioxide | 0.14 g |
| Sorbitan Monooleate 60 | 0.005 g |
| Polyethyleneglycol 6000 | 0.01 g |
| Glycerol-tris-12-hydroxystearate | 0.06 g |
| Mannitol | 1.45 g |
| Potato starch | 0.04 g |
| Polyvinylpyrrolidone | 0.09 g |

A mixture of a portion of antacid (between 50% and 70% is mixed with the hydrophobic silicon dioxide and granulated as described in Example 1. The remainder of the antacid (up to 30–50% of total amount) is blended with an equal weight of mannitol, potato starch is added, and the mixture is kneaded using a 6% aqueous solution of polyvinylpyrrolidone as granulating liquid.

The two granulates are mixed with a granulate of mannitol prepared as described in Example 2, flavour and lubricating agents are added, and the product is finally pressed into chewable tablets.

Utilising the above process, tablets containing 1.5 g of hydrotalcite or magaldrate can be prepared.

The long lasting antacid effect of these preparations has been demonstrated by a modification of Fordran's test (Fordtran, J. S., Morawski, S. G., Richardson, C. T., New Engl. J. Med. 288, 923 (1973)) comparing the pure antacid with the formulations using the same amount of antacid in each case.

The modification consists of delaying the time of the first addition of gastric juice until the pharmaceutical composition had spontaneously disintegrated in a volume of up to 15 ml of distilled water. At this point the addition of synthetic gastric juice was commenced.

In this test the following results were obtained:

| Pure Almagate | | Tablets prepared according to Example 3 |
| --- | --- | --- |
| Sample Weight | 1.5 g | 3.295 g (equivalent to 1.5 g of Almagate) |
| pH at 10 min (after the first addition of 150 ml gastric juice) | 4.70 | 4.98 |
| Time above pH 3 | 68 min | 115 min |
| Volume of HCL (0.079N) consumed | 520.30 ml | 527.02 ml |

The coated product has a longer duration of action, i.e. a 1.7 times higher than that observed with the pure antacid.

The products of this invention have an "in vitro" bioavailability similar to that of the pure antacid, (Moragues, J., Beneyto, J. E. Fabregas, J. L., Spickett, R. G. W, Arzneim. Forsch., 34 (11), 10 a, 1346 (1984)).

The floating characteristics and prolonged gastric residence time with sustained acid neutralisation have been demonstrated in human volunteer studies using isotope labelled Almagate (scintigraphy).

In normal volunteers the time required for emptying 20% of the labelled antacid from the stomach is almost 3 times longer for coated Almagate than for the uncoated product. The latter empties with the liquid phase of a light standard meal whereas emptying of the former occurs much later with a half-life of 4 hours.

We claim:

1. A solid pharmaceutical preparation comprising an internal phase and a solid external phase,
   a) the internal phase being a powder mixture comprising discrete solid granules of an antacid means for neutralizing acid and a pharmaceutically acceptable excipient,
   b) the internal phase being surrounded by a solid external phase comprising a hydrophobic organic means for floating selected from the group consisting of hydrogenated mono-, di- and tri-glycerides, wherein about 70% to 90% by weight of ester is a 12-hydroxysteric ester and about 10 to 20% by weight of ester is a stearic acid ester, a hydroxylated polyalkene having a molecular weight between about 950 and about 10,000, and a non-ionic emulsifier comprising a polyoxyethylene-sorbitan mono-ester of an oleic, lauric, stearic or palmitic acid.

2. A preparation according to claim 1, wherein the antacid means for neutralizing acid is selected from the group consisting of aluminum magnesium hydroxycarbonates and sulphates.

3. A preparation according to claim 1 in the form of a powder, granulate or chewable tablet.

4. A solid pharmaceutical preparation consisting essentially of an internal phase and a solid external phase,
   a) said internal phase comprising an antacid means for neutralizing acid and a pharmaceutically acceptable excipient, and
   b) the internal phase being surrounded by a solid external phase comprising a hydrophobic organic means for floating selected from the group consisting of hydrogenated mono-, di- and tri-glyceride, wherein about 70 to 90% by weight of ester is a 12-hydroxystearic ester and about 10 to 30% by weight of ester is a stearic acid ester, a hydroxylated polyalkene having a molecular weight between about 950 and about 10,000, and a non-ionic emulsifier comprising a polyoxyethylene-sorbitan mono-ester of an oleic, lauric, stearic or palmitic acid.

5. A solid pharmaceutical preparation comprising an internal phase and a solid external phase,
   a) the internal phase being a powder mixture of discrete solid granules of an antacid means for neutralizing acid selected from the group consisting of aluminum magnesium hydroxycarbonates and sulphates and a pharmaceutically acceptable excipient,
   b) the internal phase being surrounded by a solid external phase comprising a hydrophobic organic means for floating selected from hydrogenated mono-, di- or tri-glycerides, in which from about 70 to 90% by weight of the ester is a 12-hydroxysteric ester and about 10 to 30% by weight of ester is a stearic acid ester, a hydroxylated polyalkene having a molecular weight between about 950 and 10,000, and a non-ionic emulsifier.

6. A preparation according to claim 5 in the form of a powder, granulate or chewable tablet.

7. A solid pharmaceutical preparation comprising an internal phase and a solid external phase,
   a) the internal phase being a powder mixture comprising discrete solid granules of an antacid means for neutralizing acid, a gastric acid secretion inhibitor selected from the group consisting of cimetidine, ranitidine and omeprazole, and a pharmaceutically acceptable excipient,
   b) the internal phase being surrounded by a solid external phase comprising a hydrophobic organic means for floating selected from the group consisting of hydrogenated mono-, di- or tri-glycerides, wherein about 70 to 90% by weight of the ester is a 12-hydroxysteric ester and about 10 to 30% by weight of ester is a stearic acid ester, a hydroxylated polyalkene having a molecular weight between about 950 and about 10,000, and a non-ionic emulsifier comprising a polyoxyethylene-sorbitan mono-ester of an oleic, lauric, stearic or palmitic acid.

8. A solid pharmaceutical preparation comprising an internal phase and a solid external phase,
   a) the internal phase being a powder mixture of discrete solid granules of an antacid means for neutralizing acid selected from the group consisting of aluminum magnesium hydroxycarbonates and sulphates, a gastric acid secretion inhibitor selected from the group consisting of cimetidine, ranitidine and omeprazole, and a pharmaceutically acceptable excipient,
   b) the internal phase being surrounded by a solid external phase comprising a hydrophobic organic means for floating selected from hydrogenated mono-, di- or tri-glycerides in which from about 70 to 90% by weight of the ester is a 12-hydroxysteric ester and about 10 to 30% by weight of ester is a stearic acid ester, a hydroxylated polyalkene having a molecular weight between about 950 and 10,000, and a non-ionic emulsifier.

9. A solid pharmaceutical preparation comprising an internal phase and a solid external phase,
   a) the internal phase being a powder mixture comprising discrete solid granules of an antacid means for neutralizing acid and a pharmaceutically acceptable excipient,
   b) the internal phase being surrounded by a solid external phase consisting essentially of a hydrophobic organic means for floating selected from the group consisting of hydrogenated mono-, di- or tri-glycerides, wherein about 70 to 90% by weight of ester is a 12-hydroxysteric ester and about 10 to 30% by weight of ester is a stearic acid ester, a hydroxylated polyalkene having a molecular weight between about 950 and 10,000, and a non-ionic emulsifier comprising a polyoxyethylene-sorbitan mono-ester of an oleic, lauric, stearic or palmitic acid.

10. A solid pharmaceutical preparation comprising an internal phase and a solid external phase,
   a) the internal phase being a powder mixture of discrete solid granules of an antacid means for neutralizing acid selected from the group consisting of aluminum magnesium hydroxycarbonates and sulphates and a pharmaceutically acceptable excipient,
   b) the internal phase being surrounded by a solid external phase consisting essentially of a hydrophobic organic means for floating selected from hydrogenated mono-, di- or tri-glycerides, in which from about 70 to 90% by weight of the ester is a 12-hydroxystearic ester and about 10 to 30% by weight of ester is a stearic acid ester, a hydroxylated polyalkene having a molecular weight between about 950 and 10,000, and a non-ionic emulsifier.

* * * * *